United States Patent [19]

Bernstein

[11] Patent Number: 5,508,034

[45] Date of Patent: Apr. 16, 1996

[54] METHOD AND COMPOSITION FOR TREATING AND PREVENTING DRY SKIN DISORDERS

[75] Inventor: Joel E. Bernstein, Deerfield, Ill.

[73] Assignee: GenDerm Corporation, Lincolnshire, Ill.

[21] Appl. No.: 326,034

[22] Filed: Oct. 19, 1994

Related U.S. Application Data

[63] Continuation-in-part of Ser. No. 109,148, Aug. 19, 1993, abandoned, which is a continuation of Ser. No. 994,183, Dec. 21, 1992, abandoned, which is a continuation of Ser. No. 751,610, Aug. 21, 1991, abandoned, which is a continuation of Ser. No. 542,632, Jun. 22, 1990, abandoned, which is a continuation of Ser. No. 231,848, Aug. 12, 1988, abandoned.

[51] Int. Cl.⁶ ...................................................... A61K 7/00
[52] U.S. Cl. .............................. 424/401; 514/78; 514/847
[58] Field of Search .................................. 426/401, 450; 514/77, 78, 841

[56] References Cited

U.S. PATENT DOCUMENTS

| | | | |
|---|---|---|---|
| 4,246,285 | 1/1981 | Van Duzee | 424/358 |
| 4,760,096 | 7/1988 | Sakai | 514/847 |
| 5,294,444 | 3/1994 | Nakamura | 424/401 |
| 5,310,556 | 5/1994 | Ziegler | 424/401 |
| 5,368,857 | 11/1994 | Corcoran | 424/401 |

Primary Examiner—Gollamudi S. Kishore

[57] ABSTRACT

A method and composition for treating and preventing dry skin includes a lipid concentrate blended from a combination of the three naturally-occurring lipid groups found in the stratum corneum. The concentrate may be applied topically as prepared, or may be blended with a therapeutically acceptable vehicle suitable for topical application.

17 Claims, No Drawings

METHOD AND COMPOSITION FOR TREATING AND PREVENTING DRY SKIN DISORDERS

This is a continuation-in-part of application Ser. No. 08/109,148 filed on Aug. 19, 1993; now abandoned, which is a continuation of U.S. Ser. No. 07/994,183, filed Dec. 21, 1992, now abandoned; which is a continuation of U.S. Ser. No. 07/751,610, filed Aug. 21, 1992, now abandoned; which is a continuation of U.S. Ser. No. 07/542,632, filed Jun. 22, 1990, now abandoned; which is a continuation of U.S. Ser. No, 07/231,848, filed Aug. 12, 1988, now abandoned.

This invention relates generally to dermatological preparations and, more particularly, to methods and compositions for treating and preventing dry skin.

BACKGROUND OF THE INVENTION

Dry skin, also known as xerosis or asteatosis, affects millions of Americans each year. Attempts to treat or prevent dry skin have led to the development of a large assortment of skin creams and lotions. All of these creams and lotions have been developed from either the point of view that applying an occlusive lipid such as petrolatum or mineral oil can retard moisture loss from the skin, or that the incorporation of water-soluble materials, such as free amino acids, organic acids, inorganic ions or urea, into the cream, ointment, gel or lotion can trap or retain water in the skin.

It has been demonstrated over the last few years that the stratum corneum of the skin contains certain lipids which may form complicated layers within the stratum corneum thus forming a "water barrier" which prevents water loss from the skin. It has been discovered that formulations may be prepared composed of components of the skin's natural water barrier forming lipid complex and that when these formulations are used by themselves or when they are incorporated into creams, ointments, gels and lotions, the resulting products provide unsurpassed protection against and treatment for dry skin conditions.

In preparing the formulations disclosed herein, combinations of components from three separate classes of lipids occurring naturally in the stratum corneum can be utilized: (1) fatty acids, in either the free acid form or as triglycerides; (2) sterols and sterol esters; and (3) phospholipids and glycolipids.

SUMMARY OF THE INVENTION

The present invention provides an improved method and composition for prophylaxis for or treatment of dry skin, consisting of preparing a formulation composed of representative lipids from the three classes of lipids naturally found in the stratum corneum. Such a formulation may be applied directly or may be incorporated into a cream, ointment, gel or lotion and the resulting product applied in order to prevent or treat dryness of the skin.

DETAILED DESCRIPTION OF PREFERRED EMBODIMENTS

While other lipids may be utilized, the following members of the three classes of stratum corneum lipids combined under this invention have been successfully utilized:

1. Fatty acids: arachidonic, linoleic, linolenic, palmitic, stearic, oleic and docosanoic, all of which may be present in the inventive composition in either the free acid form or as triglycerides;
2. Sterols: cholesterol, which may be present in the inventive composition as either the sterol or as an ester, such as cholesterol sulfate; and
3. Phospholipids and glycolipids: ceramides, cephalin, and lecithin.

It is to be understood that the invention also encompasses the use of other lipids within these three classes and which occur naturally in the stratum corneum, and further encompasses the use of the naturally occurring fatty acids in either their free acid form or as triglycerides, and the naturally occurring sterols in either the sterol form or as esters. The proportions of the three classes vary in selected lipid concentrate formulations but generally fall within the following ranges:

Fatty acids: 25 to 75%
Sterols and sterol esters: 10 to 40%
Phospholipids and glycolipids: 5 to 40%

The resulting lipid concentrate formulation may then be added to cream, ointment, gel or lotion vehicles in weight/weight concentrations ranging from about 1% to about 50%. The following examples further illustrate the invention:

EXAMPLE 1

A therapeutic skin formula to treat and prevent dry skin was formulated by adding 15 gm of a lipid concentrate composed of 30% W/W cholesterol (obtained under the trade designation Loralan-CH from the Lanaetex Products, Inc., Elizabeth, N.J.), 20% W/W lecithin (obtained from American Lecithin Company, Inc., Atlanta, Ga.), and 50% W/W of a mixture of linoleic acid, linolenic acid and arachidonic acid (obtained under the trade designation of EFA complex from Phillip Rockley, Ltd., New York, N.Y.) to a lotion base as follows:

| | | |
|---|---|---|
| Isopropyl Myristate | 5.0% | 7.5 gm |
| Cetyl Alcohol | 2.0% | 3.0 gm |
| Glyceryl Stearate and PEG-100 Stearate (Arlacel 165) | 5.0% | 7.5 gm |
| Benzyl Alcohol | 1.0% | 1.5 gm |
| Lipid Concentrate | 10.0% | 15.0 gm |
| 70% Sorbitol solution | 25.0% | 37.5 gm |
| Distilled Water | 52.0% | 78.0 gm |
| TOTAL | 100.0% | 150.0 gm |

This formulation was applied to the dry skin of a 44 year old male and produced noticeably softer more supple skin after only one application.

EXAMPLE 2

A therapeutic moisturizing formulation was prepared consisting of a lipid concentrate containing 10 ml of linoleic acid (obtained from Emery Industries, Cincinnati, Ohio), 10 ml linolenic acid (obtained from Fluka Chemical Corporation, Ronkonkoma, N.Y.), 10 gm of a mixture of lecithin, cephalin and lipositol (obtained under the trade designation of Asolectin from Fluka Chemical Corporation, Ronkonkoma, N.Y.), and 10 gm of cholesterol (obtained under the trade designation of Loralan-CH from the Lanaetex Products, Inc., Elizabeth, N.J.). The resulting mixture was blended to make a cream composed as follows:

| | | |
|---|---|---|
| Isopropyl Myristate | 5.0% | 7.5 gm |
| Cetyl Alcohol | 3.0% | 4.5 gm |
| Glyceryl Stearate and | 5.0% | 7.5 gm |

| | | |
|---|---|---|
| PEG-100 Stearate (Arlacel 165) | | |
| Benzyl Alcohol | 1.0% | 1.5 gm |
| Lipid Concentrate | 5.0% | 7.5 gm |
| 70% Sorbitol solution | 25.0% | 37.5 gm |
| Distilled Water | 56.0% | 84.0 gm |
| TOTAL | 100.0% | 150.0 gm |

This formulation was applied to the dry skin on the lower legs of a 43 year old woman. Within 24 hours of twice daily application the treated skin was noticeably softer, more moist and supple.

Tests were also performed to assess the efficacy of the present invention in preventing water loss. Baseline measurements of 15 healthy adult test subjects were performed to determine the barrier-forming properties of different formulations of the present invention, and to compare these properties with those of two commercially-available skin creams, Eucerin*, manufactured by Beiersdorf, Inc., Norwalk, Conn., and Moisturel*, manufactured by Westwood Pharmaceuticals, Inc., Buffalo, N.Y. A Servo Med Evaporimeter was used to measure rate of water loss from a 4.9 cm$^2$ patch of unprotected skin. Thereafter, formulations of the present invention were applied to the test subjects at separate 4.9 cm$^2$ test sites, as were applications of Eucerin* and Moisturel* skin creams. Each application consisted of 25 microliters of each formulation.

Lipid Concentrate I consisted of 30% w/w of cholesterol, 20% w/w of lecithin and ceramides, and 50% w/w of the linoleic, linolenic and arachidonic acid mix. Lipid Concentrate II consisted of 15% w/w of cholesterol, 10% w/w lecithin and ceramides, and 75% w/w of the linoleic, linolenic and arachidonic acid mix.

The formulations tested were prepared as follows:

FORMULA I

| | Percent by weight |
|---|---|
| Isopropyl Myristate | 5.0 |
| Cetyl Alcohol | 3.0 |
| Arlacel 165 | 5.0 |
| Benzyl Alcohol | 1.0 |
| Lipid Concentrate II | 10.0 |
| 70% Sorbitol Solution | 25.0 |
| Distilled Water | 51.0 |
| TOTAL | 100.0 |

FORMULA 2

| | Percent by weight |
|---|---|
| Isopropyl Myristate | 5.0 |
| Cetyl Alcohol | 3.0 |
| Arlacel 165 | 5.0 |
| Benzyl Alcohol | 1.0 |
| Lipid Concentrate II | 5.0 |
| 70% Sorbitol Solution | 25.0 |
| Distilled Water | 56.0 |
| TOTAL | 100.0 |

FORMULA 3

| | Percent by weight |
|---|---|
| Isopropyl Myristate | 5.0 |
| Cetyl Alcohol | 3.0 |
| Arlacel 165 | 5.0 |
| Benzyl Alcohol | 1.0 |
| Lipid Concentrate II | 10.0 |
| Vitamin E | 1.0 |
| 70% Sorbitol Solution | 25.0 |
| Distilled Water | 500 |
| TOTAL | 100.0 |

Water loss measurements showed that all five formulations tested reduced water loss as compared to the untreated site, with the formulations of the present invention establishing a stronger barrier to water loss than the commercially available preparations. The test results were as follows:

| | % change in evaporative water loss |
|---|---|
| Formula 1 | 3.4 |
| Formula 2 | 3.5 |
| Formula 3 | 3.6 |
| Eucerin ® | 3.7 |
| Moisturel ® | 3.9 |
| Untreated Site | 4.5 |

While the foregoing has presented specific embodiments of the present invention, it is to be understood that these embodiments have been presented by way of example only. It is expected that others will perceive variations which, while varying from the foregoing, do not depart from the spirit and scope of the invention as herein described and claimed. For example, the invention encompasses lipids within the three classes and naturally occurring within the stratum corneum other than those used in the particular Examples herein, and further encompasses the use of the naturally occurring fatty acids in either their free acid form or as triglycerides, and the use of the naturally occurring sterols in either the sterol form or as esters. None of the foregoing is attempted to in any manner limit the scope of the present invention.

What is claimed is:

1. A method of preventing or treating dry skin for one in need thereof, said method comprising applying topically to said skin a composition comprising a concentrate of naturally occurring stratum corneum lipids, said concentrate comprising:

(a) a mixture of naturally occurring stratum corneum free fatty acids or triglyceride forms of said fatty acid mixtures in a proportion of about 25% to about 75% by weight of concentrate;

(b) naturally occurring stratum corneum cholesterol or esters of said cholesterol in a proportion of about 10% to about 40% by weight of concentrate; and (c) One or more naturally occurring stratum corneum lipids selected from the group consisting of ceramide, lecithin and cephalin in a proportion of about 5% to about 40% by weight of concentrate.

2. The method of claim 1 wherein said fatty acids are selected from the group consisting of arachidonic acid, linoleic acid, linolenic acid, palmitic acid, stearic acid, oleic acid, and docosanoic acid.

3. The method of claim 1 wherein said cholesterol is cholesterol sulfate.

4. The method of claim 1 wherein said concentrate is incorporated into a pharmaceutically acceptable vehicle topical application prior to the topical application thereof to the skin.

5. A lipid concentrate, said concentrate comprising at least one constituent from each of the following groups:
   (a) a mixture of naturally-occurring stratum corneum free fatty acids or triglyceride forms of said fatty acids being present in a proportion of about 25% to about 75% by weight of concentrate;
   (b) naturally occurring stratum corneum cholesterol or esters of said cholesterol, said cholesterol or esters thereof being present in a proportion of about 10% to about 40% by weight of concentrate; and
   (c) naturally occurring stratum corneum lipids being selected from the group consisting of ceramide, lecithin and cephalin and present in a proportion from about 5% to about 40% by weight of concentrate.

6. The composition of claim 5 where said fatty acids are selected from the group consisting of arachidonic acid, linoleic acid, linolenic acid, palmitic acid, stearic acid, oleic acid, and docosanoic acid.

7. The composition of claim 5 wherein said cholesterol is cholesterol sulfate.

8. A composition comprising the lipid concentrate of claim 5 and a pharmaceutically acceptable vehicle suitable for topical application of said concentrate.

9. The composition of claim 8 wherein said vehicle is selected from the group of creams, gels, lotions and ointments.

10. The composition of claim 8 wherein said lipid concentrate is present in a weight proportion of about 1% to about 50%.

11. The composition of claim 10 wherein said lipid concentrate is present in a weight proportion of about 5% to 10%.

12. The composition of claim 8 wherein said lipid concentrate comprises, by weight, about 30% cholesterol, about 20% lecithin and about 50% of a mixture of linoleic acid, linolenic acid and arachidonic acid.

13. The composition of claim 12 wherein said lipid concentrate is present in a weight proportion of about 1% to about 50%.

14. The composition of claim 13 wherein said lipid concentration is present in a weight proportion of about 5% to about 10%.

15. The composition of claim 8 wherein said lipid concentrate comprises, by weight, about 15% cholesterol, about 10% lecithin and ceramides, and about 75% linoleic, linolenic and arachidonic acids.

16. The composition of claim 15 wherein said lipid concentrate is present in a weight proportion of about 1% to about 50 %.

17. The composition of claim 16 wherein said lipid concentrate is present in a weight proportion of about 5% to about 10%.

* * * * *